US00PP36947P2

(12) United States Plant Patent
Schoone

(10) Patent No.: US PP36,947 P2
(45) Date of Patent: Sep. 9, 2025

(54) ***PHALAENOPSIS* PLANT NAMED 'Soundtrack'**

(50) Latin Name: *Phalaenopsis hybrida*
Varietal Denomination: Soundtrack

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 19/171,336

(22) Filed: Apr. 6, 2025

Related U.S. Application Data

(60) Provisional application No. 63/575,712, filed on Apr. 6, 2024.

(51) Int. Cl.
*A01H 6/62* (2018.01)
*A01H 5/02* (2018.01)

(52) U.S. Cl.
USPC ..... Plt./311

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Phalaenopsis* plant named 'Soundtrack', characterized by its upright plant habit; strong flowering stems; healthy and sturdy leaves; freely flowering habit with typically two inflorescences developing per plant, each inflorescence with numerous flowers; "big lip" type flowers with petals and sepals that are dark purplish red in color with light purple-colored margins, and labella that are dark purplish red and light purple in color with reddish purple-colored venation; and good postproduction longevity.

2 Drawing Sheets

Figure 1:
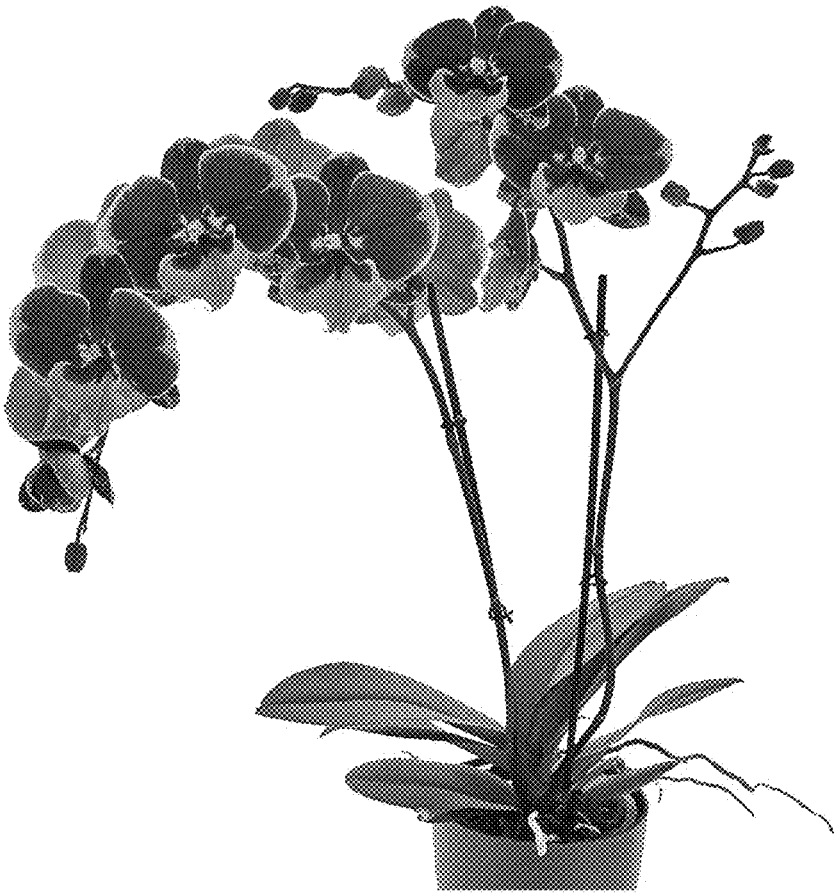

Botanical designation: *Phalaenopsis hybrida.*
Cultivar denomination: 'SOUNDTRACK'.

CROSS-REFERENCED TO CLOSELY-RELATED APPLICATIONS

Title: Varieties of *Phalaenopsis* Plants
Inventor: René Schoone
Filed: Apr. 6, 2024
Ser. No. 63/575,712

Inventor and Applicant/Assignee hereby claims the benefit of this provisional U.S. Patent Application.

A European Community Plant Breeder's Rights application for the instant plant was filed by the Applicant/Assignee, Floricultura B.V. of Heemskerk, The Netherlands on Jul. 11, 2024, application number 2024/1649. Foreign priority is not claimed to this application.

BACKGROUND OF THE INVENTION

The present invention relates to a new and distinct cultivar of *Phalaenopsis* plant, botanically known as *Phalaenopsis hybrida*, and hereinafter referred to by the name 'Soundtrack'.

The new *Phalaenopsis* plant is a product of a planned breeding program conducted by the Inventor in Assendelft and Heemskerk, The Netherlands. The objective of the breeding program is to develop new fast-growing and freely flowering *Phalaenopsis* plants with good leaf shape and flowers with unique and attractive patterns and coloration.

The new *Phalaenopsis* plant originated from a cross-pollination in September 2014 in Assendelft, The Netherlands of a *Phalaenopsis hybrida* 'Chian Xen Pearl', not patented, as the female, or seed, parent with *Phalaenopsis hybrida* 'K.S. Big Class', not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in September 2020.

Asexual reproduction of the new *Phalaenopsis* plant by in vitro meristem propagation in a controlled environment in Assendelft, The Netherlands since September 2021 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Soundtrack'. These characteristics in combination distinguish 'Soundtrack' as a new and distinct *Phalaenopsis* plant:

1. Upright plant habit.
2. Strong flowering stems.
3. Healthy and sturdy leaves.
4. Freely flowering habit with typically two inflorescences developing per plant, each inflorescence with numerous flowers.

5. "Big lip" type flowers with petals and sepals that are dark purplish red in color with light purple-colored margins, and labella that are dark purplish red and light purple in color with reddish purple-colored venation.
6. Good postproduction longevity.

Plants of the new *Phalaenopsis* can be compared to plants of the female parent, 'Chian Xen Pearl'. Plants of the new *Phalaenopsis* differ primarily from plants of 'Chian Xen Pearl' in flower type as flowers of plants of the new *Phalaenopsis* are "big lip" types whereas flowers of plants of 'Chian Xen Pearl' are not "big lip" types.

Plants of the new *Phalaenopsis* can be compared to plants of the male parent, 'K.S. Big Class'. Plants of the new *Phalaenopsis* differ primarily from plants of 'K.S. Big Class' in flower petal main color as the main color of the flower petals of plants of the new *Phalaenopsis* is dark purplish red whereas the main color of the flower petals of plants of 'K.S. Big Class' is violet.

Plants of the new *Phalaenopsis* can be compared to plants of x *Doritaenopsis* (*Doritis* x *Phalaenopsis*) 'Untold Stories', disclosed in U.S. Plant Pat. No. 34,022. In side-by-side comparisons, plants of the new *Phalaenopsis* differ primarily from plants of 'Untold Stories' in the following characteristics:

1. Plants of the new *Phalaenopsis* are taller than plants of 'Untold Stories'.
2. Flowers of plants of the new *Phalaenopsis* broader than flowers of plants of 'Untold Stories'.
3. Flower petals of plants of the new *Phalaenopsis* are free whereas flower petals of plants of 'Untold Stories' are touching.
4. The new *Phalaenopsis* and 'Untold Stories' differ in flower petal color as the ground color of flower petals of plants of the new *Phalaenopsis* is dark reddish purple whereas the ground color of the flower petals of 'Untold Stories' is white.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Soundtrack' grown in a container.

Figure 2:
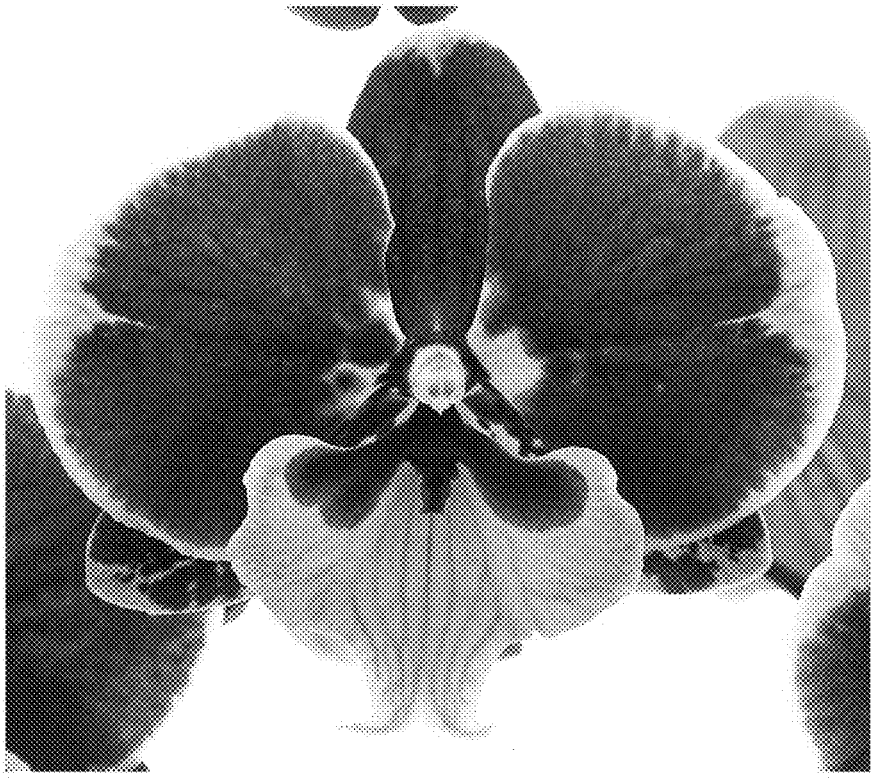

The photograph on the second sheet (FIG. 2) is a close-up view of a typical flower of 'Soundtrack'.

DETAILED BOTANICAL DESCRIPTION

The aforementioned photographs and following observations and measurements describe plants grown during the summer in 11-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final months of production of the plants, day temperatures ranged from 20° C. to 22° C. and night temperatures ranged from 18° C. to 20° C. During the production of the plants, light levels ranged from a minimum of 5 klux to a maximum of 10 klux. In the following description, color references are made to The Royal Horticultural Society Colour Chart, 2015 Edition, except where general terms of ordinary dictionary significance are used.

Botanical classification: *Phalaenopsis hybrida* 'Soundtrack'.

Parentage:

*Female, or seed, parent.*—*Phalaenopsis hybrida* 'Chian Xen Pearl', not patented.

*Male, or pollen, parent.*—*Phalaenopsis hybrida* 'K.S. Big Class', not patented.

Propagation:

*Type.*—By in vitro meristem propagation.

*Time to initiate roots, summer and winter.*—About two weeks at temperatures about 28° C. to 30° C.

*Time to produce a rooted young plant, summer and winter.*—About 20 to 25 weeks at temperatures about 28° C. to 30° C.

*Root description.*—Thin, fibrous; typically light yellowish white in color; actual color of the roots is dependent on substrate composition, water quality, fertilizer, substrate temperature and age of roots.

*Rooting habit.*—Freely branching; medium density.

Plant description:

*Plant form and growth habit.*—Herbaceous epiphyte; upright plant habit with typically two inflorescences developing per plant, each inflorescence with numerous flowers; monopodial; moderately vigorous growth habit and moderate growth rate.

*Plant height, substrate level to top of foliar plane.*—About 11.9 cm.

*Plant height, substrate level to top of floral plane.*—About 43.5 cm.

*Plant diameter or spread.*—About 34.9 cm.

Leaf description:

*Arrangement and quantity.*—Distichous, simple; sessile; about six to seven fully-developed leaves per plant.

*Length.*—About 18.2 cm.

*Width.*—About 7 cm.

*Aspect.*—Semi-erect and somewhat outwardly arching.

*Shape.*—Narrowly elliptic to obovate-elliptic or ovate-elliptic; slightly carinate.

*Apex.*—Unequal acute to unequal obtuse.

*Base.*—Sheathing. Sheath length: About 1.7 cm. Sheath width: About 1.2 cm. Sheath color, upper and lower surfaces: Close to a blend of 143A and 143B; distal margins, close to N199A and N199B.

*Margin.*—Entire.

*Texture and luster, upper and lower surfaces.*—Smooth, glabrous; slightly glossy.

*Venation pattern.*—Camptodromous.

*Color.*—Developing leaves, upper surface: Close to NN137B; at the base, close to a blend of N186C and 200A. Developing leaves, lower surface: Close to 146B strongly tinged with close to N186C; marginal edges, close to N186C. Fully expanded leaves, upper surface: Close to NN137B; venation, close to 147A. Fully expanded leaves, lower surface: Close to 146B variably tinged with close to N186C and a blend of N186C and 187A; marginal edges, close to a blend of N186C and 187A; venation, close to 144C and N187A.

Inflorescence description:

*Appearance and flowering habit*.—Showy zygomorphic flowers arranged on axillary simple or branched racemes; typically two inflorescences develop per plant; each inflorescence with about eleven flowers; flowers face mostly outwardly on outwardly arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity and postproduction longevity*.—Long flowering period and good postproduction longevity, individual flowers maintain good substance for about seven weeks on the plant; flowers not persistent.

*Inflorescence length* (*lowermost flower to inflorescence apex*).—About 28.9 cm.

*Inflorescence width*.—About 13.1 cm.

*Flower buds*.—Height: About 2.1 cm. Diameter: About 1.4 cm by 1.4 cm. Shape: Narrowly ovate to close to ovoid. Color: Close to 197C; proximally, strongly tinged with close to 186A; venation, close to 183C.

*Flower size*.—About 8.2 cm (vertical) by 9 cm (horizontal).

*Flower depth*.—About 2.2 cm.

*Petals, quantity and arrangement*.—Three, two lateral petals and one center petal transformed into a labellum.

*Lateral petals*.—Length: About 4.2 cm. Width: About 5.2 cm. Shape: Broadly reniform; not fused. Apex: Broadly and shallowly retuse. Margin: Entire to slightly and irregularly angulate; occasionally a single and random shallow incision. Texture and luster, upper and lower surfaces: Smooth, glabrous; velvety; matte. Color: When opening, upper surface: Close to N186D, 187B and a blend of N186D and 187B; towards the margins, close to N78D with narrow marginal edges, close to 76D; at the base, small blotch, close to NN155D. When opening, lower surface: Close to 76A; towards the apex, tinged with close to NN78D; fine blotches, close to N75A to N75C; towards the base, close to N155A; venation, close to 77A and 77B. Fully opened, upper surface: Close to N79C, N186D and a blend of N79C and N186D; towards the margins, close to N75B with narrow marginal edges, close to 76B, 76C and NN155D; at the base, small blotch, close to NN155D; colors do not change with subsequent development. Fully opened, lower surface: Close to 76A overlain with close to N187D; fine blotches, close to N75A to N75C; towards the center, close to 76C; venation, close to 75A; colors do not change with subsequent development.

*Labella*.—Appearance: Lateral and central lobes fused forming a "big lip" type labella. Length: About 4.4 cm. Width: About 4.6 cm. Shape: Rhomboidal-deltoid in overall outline; moderately concave. Apex: Cleft with two cirrhose apices. Margins: Entire. Texture and luster, upper and lower surfaces: Smooth, glabrous, moderately velvety; matte. Callosities: Located at the base of the labellum and attachment point of the lateral petals; about 9 mm in length, about 4 mm in width and about 8 mm in height. Color: When opening, upper surface: Close to a blend of N78C and N78D; blotches, close to 84C; towards the base, close to N186D and 187C; venation, close to NN78B and NN78C. When opening, lower surface: Close to N78C; towards the base, close to a blend of 156D and N187D; venation, close to N78A and N78B. Fully opened, upper surface: Close to a blend of N75C and N78D; towards the base, close to N186D slightly tinged with close to N79C; venation, close to NN78B. Fully opened, lower surface: Close to a blend of N75B and N80D; towards the base, close to N187D slightly tinged with close to 76B; venation, close to NN78C. Color, callosities: When developing: Close to 187C and 75A; at the apex, close to 187C. Fully developed: Close to N186D and a blend of close to 76C and 76D; at the apex, close to N78A.

*Sepals*.—Quantity and arrangement: Three, one upper dorsal sepal and two lower lateral sepals. Length, dorsal sepal: About 4.4 cm. Width, dorsal sepal: About 2.9 cm. Length, lateral sepals: About 4.4 cm. Width, lateral sepals: About 2.5 cm. Shape, dorsal sepal: Ovate-elliptic. Shape, lateral sepals: Ovate. Apex, dorsal sepal: Obtuse to shallowly retuse. Apex, lateral sepals: Broadly acute. Base, dorsal and lateral sepals: Truncate. Margins, dorsal and lateral sepals: Entire. Texture and luster, dorsal and lateral sepals, upper and lower surfaces: Smooth, glabrous; moderately velvety; matte. Color, dorsal sepal: When opening, upper surface: Close to 187B; towards the apex, close to 187C and at the apex, close to N78C with narrow marginal edges, close to 76D; venation, close to N186A. When opening, lower surface: Close to 197D tinged with close to 76D; towards the apical margins, close to N75A with narrow marginal edges, close to 84D; venation, close to NN78B. Fully opened, upper surface: Close to N79C, N186D and a blend of N79C and N186D; apical margins, close to 76C and 76D; venation, close to N186A. Fully opened, lower surface: Close to 76C; centers, close to 186C; apical margins, close to N75A with narrow marginal edges, close to 84D; venation, close to N78C. Color, lateral sepals: When opening, upper surface: Close to 187B and 187C; blotches, close to 75B to 75D; at the apex, close to N78C and N78D; venation, close to N186A. When opening, lower surface: Close to 186C; towards the apex, close to 70B tinged with close to 160D; venation, close to 71A. Fully opened, upper surface: Close to 186D; towards the base, close to 187B with blotches, close to 76B and 76C; at the apex, close to N78D. Fully opened, lower surface: Close to N75C; towards the apex, close to N75A; venation, close to N78B.

*Peduncles*.—Length: About 52.7 cm. Diameter: About 4.5 mm. Strength: Strong. Aspect: Upright to outwardly arching. Texture and luster: Smooth, glabrous; matte. Color: Close to a blend of 147A and N200A densely covered with fine dots, close to 146B.

*Pedicels*.—Length: About 3.7 cm. Diameter: About 3 mm. Strength: Moderately strong. Aspect: About 55° from peduncle axis. Texture and luster: Smooth, glabrous; matte. Color: Close to a blend of N148D and 197C; distal end, close to N75A; proximal end, close to 147A tinged with close to N186C.

*Reproductive organs*.—Androecium: Column length: About 9 mm. Column width: About 6 mm. Column color: Close to NN155A with blotches, close to N78C. Pollinia quantity: Two. Pollinia diameter (per two pollinia): About 2.5 mm. Pollinia color: Close to 17A. Gynoecium: Stigma length: About 3 mm. Stigma width: About 4 mm. Stigma shape: Reniform. Stigma color: Close to N155A. Ovary length: About 5 mm. Ovary diameter: About 1 mm. Ovary color: Close to 150D. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'Soundtrack' as herein illustrated and described.

* * * * *